United States Patent
Dobak, III et al.

(10) Patent No.: US 8,157,794 B2
(45) Date of Patent: Apr. 17, 2012

(54) METHOD AND DEVICE FOR PERFORMING COOLING-OR CRYO-THERAPIES FOR, E.G., ANGIOPLASTY WITH REDUCED RESTENOSIS OR PULMONARY VEIN CELL NECROSIS TO INHIBIT ATRIAL FIBRILLATION

(75) Inventors: John D. Dobak, III, La Jolla, CA (US); Hans W. Kramer, Temecula, CA (US); Steven A. Yon, San Diego, CA (US)

(73) Assignee: Innercool Therapies, Inc., San Diego, CA (US)

( * ) Notice: Subject to any disclaimer, the term of this patent is extended or adjusted under 35 U.S.C. 154(b) by 1204 days.

(21) Appl. No.: 11/978,888

(22) Filed: Oct. 30, 2007

(65) Prior Publication Data
US 2008/0300585 A1    Dec. 4, 2008

Related U.S. Application Data

(60) Continuation of application No. 10/039,466, filed on Jan. 3, 2002, now Pat. No. 7,291,144, which is a division of application No. 09/516,319, filed on Mar. 1, 2000, now abandoned, which is a continuation-in-part of application No. 09/052,545, filed on Mar. 31, 1998, now Pat. No. 6,231,595, and a continuation-in-part of application No. 09/215,038, filed on Dec. 16, 1998, now Pat. No. 6,261,312.

(51) Int. Cl.
*A61B 18/02* (2006.01)
(52) U.S. Cl. ............... 606/22; 606/21; 606/23
(58) Field of Classification Search .......... 606/20–23; 607/96, 104–106
See application file for complete search history.

(56) References Cited

U.S. PATENT DOCUMENTS

| | | | |
|---|---|---|---|
| 2,308,484 A | 1/1943 | Auzin et al. |
| 2,374,609 A | 4/1945 | McCollum |
| 2,615,686 A | 10/1952 | Davidson |

(Continued)

FOREIGN PATENT DOCUMENTS

AU         730835 B2    8/1997

(Continued)

OTHER PUBLICATIONS

Lustgarten, Daniel L., et al.; "Cryothermal Ablation: Mechanism of Tissue Injury and Current Experience in the Treatment of Tachyarrhythmias"; Progress in Cardiovascular Diseases; vol. 41; No. 6; May/Jun. 1999; pp. 481-498.

(Continued)

*Primary Examiner* — Roy Gibson

(57) ABSTRACT

The present invention provides an enhanced method and device to inhibit or reduce the rate of restenosis following angioplasty or stent placement. The invention involves placing a balloon tipped catheter in the area treated or opened through balloon angioplasty immediately following angioplasty. The balloon, which can have a dual balloon structure, may be delivered through a guiding catheter and over a guidewire already in place from a balloon angioplasty. A fluid such as a perfluorocarbon may be flowed into the balloon to freeze the tissue adjacent the balloon, this cooling being associated with reduction of restenosis. The catheter may also be used to reduce atrial fibrillation by inserting and inflating the balloon such that an exterior surface of the balloon is in contact with at least a partial circumference of the portion of the pulmonary vein adjacent the left atrium.

6 Claims, 2 Drawing Sheets

U.S. PATENT DOCUMENTS

| | | | |
|---|---|---|---|
| 2,672,032 A | 3/1954 | Towse |
| 2,913,009 A | 11/1959 | Kuthe |
| 3,125,096 A | 3/1964 | Antiles at al. |
| 3,228,400 A | 1/1966 | Armao |
| 3,298,371 A | 1/1967 | Lee |
| 3,369,549 A | 2/1968 | Armao |
| 3,425,419 A | 2/1969 | Dato |
| 3,504,674 A | 4/1970 | Swenson et al. |
| 3,604,419 A | 9/1971 | Diskin et al. |
| 3,612,175 A | 10/1971 | Ford et al. |
| 3,674,031 A | 7/1972 | Weicho |
| 3,696,813 A | 10/1972 | Wallach |
| 3,786,814 A | 1/1974 | Armao |
| 3,859,986 A | 1/1975 | Okada et al. |
| 3,865,116 A | 2/1975 | Brooks |
| 3,867,294 A | 2/1975 | Pall et al. |
| 3,888,259 A | 6/1975 | Miley |
| 3,889,680 A | 6/1975 | Armao |
| 3,971,383 A | 7/1976 | Van Gerven |
| 4,038,519 A | 7/1977 | Foucras |
| 4,153,048 A | 5/1979 | Magrini |
| 4,160,455 A | 7/1979 | Law |
| 4,190,033 A | 2/1980 | Foti |
| 4,231,425 A | 11/1980 | Engstrom |
| 4,275,734 A | 6/1981 | Mitchiner |
| 4,298,006 A | 11/1981 | Parks |
| 4,318,722 A | 3/1982 | Altman |
| 4,323,071 A | 4/1982 | Simpson et al. |
| 4,427,009 A | 1/1984 | Wells et al. |
| 4,445,500 A | 5/1984 | Osterholm |
| 4,464,172 A | 8/1984 | Lichtenstein |
| 4,483,341 A | 11/1984 | Witteles |
| 4,502,286 A | 3/1985 | Okada et al. |
| 4,569,355 A | 2/1986 | Bitterly |
| 4,581,017 A | 4/1986 | Sahota |
| 4,602,642 A | 7/1986 | O'Hara et al. |
| 4,655,746 A | 4/1987 | Daniels et al. |
| 4,672,962 A | 6/1987 | Hershenson |
| 4,745,922 A | 5/1988 | Taylor |
| 4,747,826 A | 5/1988 | Sassano |
| 4,748,979 A | 6/1988 | Hershenson |
| 4,750,493 A | 6/1988 | Brader |
| 4,762,129 A | 8/1988 | Bonzel |
| 4,762,130 A | 8/1988 | Fogarty et al. |
| 4,781,033 A | 11/1988 | Steyert |
| 4,781,799 A | 11/1988 | Herbert, Jr. et al. |
| 4,820,349 A | 4/1989 | Saab |
| 4,860,744 A | 8/1989 | Johnson et al. |
| 4,883,455 A | 11/1989 | Leonard |
| 4,894,164 A | 1/1990 | Polaschegg |
| 4,904,237 A | 2/1990 | Janese |
| 4,920,963 A | 5/1990 | Brader |
| 4,951,677 A | 8/1990 | Crowley et al. |
| 4,964,409 A | 10/1990 | Tremulis |
| 5,000,734 A | 3/1991 | Boussignac et al. |
| 5,002,531 A | 3/1991 | Bonzel |
| 5,014,695 A | 5/1991 | Benak et al. |
| 5,018,521 A | 5/1991 | Campbell |
| 5,019,075 A | 5/1991 | Spears et al. |
| 5,024,668 A | 6/1991 | Peters et al. |
| 5,041,089 A | 8/1991 | Mueller et al. |
| 5,046,497 A | 9/1991 | Millar |
| 5,078,713 A | 1/1992 | Varney |
| 5,089,260 A | 2/1992 | Hunter et al. |
| 5,092,841 A | 3/1992 | Spears |
| 5,106,360 A | 4/1992 | Ishwara et al. |
| 5,106,368 A | 4/1992 | Uldall et al. |
| 5,108,390 A | 4/1992 | Potocky et al. |
| RE33,911 E | 5/1992 | Samson et al. |
| 5,110,721 A | 5/1992 | Anaise et al. |
| 5,112,438 A | 5/1992 | Bowers |
| 5,117,822 A | 6/1992 | Laghi |
| 5,147,355 A | 9/1992 | Friedman et al. |
| 5,149,321 A | 9/1992 | Klatz et al. |
| 5,150,706 A | 9/1992 | Cox et al. |
| 5,151,100 A | 9/1992 | Abele et al. |
| 5,180,364 A | 1/1993 | Ginsburg |
| 5,190,539 A | 3/1993 | Fletcher et al. |
| 5,191,883 A | 3/1993 | Lennox et al. |
| 5,196,024 A | 3/1993 | Barath |
| 5,211,631 A | 5/1993 | Sheaff |
| 5,234,405 A | 8/1993 | Klatz et al. |
| 5,236,908 A | 8/1993 | Gruber et al. |
| 5,246,421 A | 9/1993 | Saab |
| 5,248,312 A | 9/1993 | Langberg |
| 5,250,070 A | 10/1993 | Parodi |
| 5,257,977 A | 11/1993 | Eshel |
| 5,264,260 A | 11/1993 | Saab |
| 5,267,341 A | 11/1993 | Shearin |
| 5,269,369 A | 12/1993 | Faghri |
| 5,269,749 A | 12/1993 | Koturov |
| 5,269,758 A | 12/1993 | Taheri |
| 5,281,213 A | 1/1994 | Milder et al. |
| 5,281,215 A | 1/1994 | Milder |
| 5,306,261 A | 4/1994 | Alliger et al. |
| 5,310,440 A | 5/1994 | Zingher |
| 5,328,471 A * | 7/1994 | Slepian ............... 604/101.03 |
| 5,334,193 A | 8/1994 | Nardella |
| 5,337,734 A | 8/1994 | Saab |
| 5,342,301 A | 8/1994 | Saab |
| 5,344,436 A | 9/1994 | Fontenot et al. |
| 5,358,486 A | 10/1994 | Saab |
| 5,365,750 A | 11/1994 | Greenthal |
| 5,368,591 A | 11/1994 | Lennox et al. |
| 5,383,854 A | 1/1995 | Safar et al. |
| 5,383,918 A | 1/1995 | Panetta |
| 5,385,148 A | 1/1995 | Lesh et al. |
| 5,395,314 A | 3/1995 | Klatz et al. |
| 5,395,331 A | 3/1995 | O'Neill et al. |
| 5,403,281 A | 4/1995 | O'Neill et al. |
| 5,411,477 A | 5/1995 | Saab |
| 5,417,686 A | 5/1995 | Peterson et al. |
| 5,423,745 A | 6/1995 | Todd et al. |
| 5,423,807 A | 6/1995 | Milder |
| 5,433,740 A | 7/1995 | Yamaguchi |
| 5,437,673 A | 8/1995 | Baust et al. |
| 5,443,456 A | 8/1995 | Alliger et al. |
| 5,443,781 A | 8/1995 | Saab |
| 5,462,521 A | 10/1995 | Brucker et al. |
| 5,486,204 A | 1/1996 | Clifton |
| 5,486,208 A | 1/1996 | Ginsburg |
| 5,496,271 A | 3/1996 | Burton et al. |
| 5,499,973 A | 3/1996 | Saab |
| 5,520,682 A | 5/1996 | Baust et al. |
| 5,531,776 A | 7/1996 | Ward et al. |
| 5,536,247 A | 7/1996 | Thornton |
| 5,549,559 A | 8/1996 | Eshel |
| 5,554,119 A | 9/1996 | Harrison et al. |
| 5,558,644 A | 9/1996 | Boyd et al. |
| 5,569,195 A | 10/1996 | Saab |
| 5,573,532 A | 11/1996 | Chang et al. |
| 5,578,008 A | 11/1996 | Hara |
| 5,584,804 A | 12/1996 | Klatz et al. |
| 5,588,438 A | 12/1996 | McKown et al. |
| 5,591,162 A | 1/1997 | Fletcher et al. |
| 5,620,480 A | 4/1997 | Rudie |
| 5,622,182 A | 4/1997 | Jaffe |
| 5,624,392 A | 4/1997 | Saab |
| 5,630,837 A | 5/1997 | Crowley |
| 5,643,197 A | 7/1997 | Brucker et al. |
| 5,647,051 A | 7/1997 | Neer |
| 5,653,692 A | 8/1997 | Masterson et al. |
| 5,676,693 A | 10/1997 | LaFontaine |
| 5,709,654 A | 1/1998 | Klatz et al. |
| 5,713,941 A | 2/1998 | Robins et al. |
| 5,716,386 A | 2/1998 | Ward et al. |
| 5,733,280 A | 3/1998 | Avitall |
| 5,733,318 A | 3/1998 | Augustine |
| 5,733,319 A | 3/1998 | Neilson et al. |
| 5,735,809 A | 4/1998 | Gorsuch |
| 5,741,248 A | 4/1998 | Stern et al. ............... 606/21 |
| 5,755,690 A | 5/1998 | Saab |
| 5,792,140 A | 8/1998 | Tu et al. ............... 606/41 |
| 5,797,878 A | 8/1998 | Bleam |
| 5,799,661 A | 9/1998 | Boyd et al. |
| 5,800,480 A | 9/1998 | Augustine et al. |
| 5,800,483 A | 9/1998 | Vought |

| | | | | | | |
|---|---|---|---|---|---|---|
| 5,800,488 | A | 9/1998 | Crockett ................... 607/105 | 6,241,722 | B1 | 6/2001 | Dobak et al. |
| 5,800,516 | A | 9/1998 | Fine et al. | 6,245,064 | B1 | 6/2001 | Lesh et al. |
| 5,807,391 | A | 9/1998 | Wijkamp | 6,245,095 | B1 | 6/2001 | Dobak, III et al. |
| 5,820,593 | A | 10/1998 | Safar et al. | 6,248,057 | B1 | 6/2001 | Mavity et al. |
| 5,824,030 | A | 10/1998 | Yang et al. | 6,251,093 | B1 | 6/2001 | Valley et al. |
| 5,827,222 | A | 10/1998 | Klatz et al. | 6,251,129 | B1 | 6/2001 | Dobak, III et al. |
| 5,827,237 | A | 10/1998 | Macoviak et al. | 6,251,130 | B1 | 6/2001 | Dobak, III et al. |
| 5,827,269 | A | 10/1998 | Saadat | 6,253,769 | B1 | 7/2001 | LaFontaine et al. |
| 5,833,671 | A | 11/1998 | Macoviak et al. | 6,254,588 | B1 | 7/2001 | Jones et al. |
| 5,833,673 | A | 11/1998 | Ockuly et al. | 6,254,626 | B1 | 7/2001 | Dobak, III et al. |
| 5,834,465 | A | 11/1998 | Olney | 6,261,312 | B1 | 7/2001 | Dobak, III et al. |
| 5,837,003 | A | 11/1998 | Ginsburg | 6,264,679 | B1 | 7/2001 | Keller et al. |
| 5,861,021 | A | 1/1999 | Thome | 6,267,747 | B1 | 7/2001 | Samson et al. |
| 5,868,735 | A | 2/1999 | LaFontaine ................ 606/21 | 6,270,476 | B1 | 8/2001 | Santoianni et al. |
| 5,871,526 | A | 2/1999 | Gibbs et al. | 6,270,493 | B1 | 8/2001 | Lalonde et al. |
| 5,873,835 | A | 2/1999 | Hastings et al. | 6,270,494 | B1 | 8/2001 | Kovalcheck et al. |
| 5,879,316 | A | 3/1999 | Safar et al. | 6,287,326 | B1 | 9/2001 | Pecor |
| 5,879,329 | A | 3/1999 | Ginsburg | 6,290,674 | B1 | 9/2001 | Roue et al. |
| 5,899,898 | A | 5/1999 | Arless et al. | 6,290,696 | B1 | 9/2001 | LaFontaine |
| 5,899,899 | A | 5/1999 | Arless et al. | 6,290,697 | B1 | 9/2001 | Tu et al. |
| 5,901,783 | A | 5/1999 | Dobak, III et al. | 6,290,717 | B1 | 9/2001 | Phillips |
| 5,902,268 | A | 5/1999 | Saab | 6,295,990 | B1 | 10/2001 | Lewis et al. |
| 5,906,588 | A | 5/1999 | Safar et al. | 6,296,654 | B1 | 10/2001 | Ward |
| 5,906,594 | A | 5/1999 | Scarfone et al. | 6,299,599 | B1 | 10/2001 | Pham |
| 5,906,636 | A | 5/1999 | Casscells, III et al. | 6,305,378 | B1 | 10/2001 | Lesh |
| 5,913,856 | A | 6/1999 | Chia et al. | 6,306,161 | B1 | 10/2001 | Ginsburg |
| 5,913,885 | A | 6/1999 | Klatz et al. | 6,312,452 | B1 | 11/2001 | Dobak, III et al. |
| 5,913,886 | A | 6/1999 | Soloman | 6,325,818 | B1 | 12/2001 | Werneth |
| 5,916,242 | A | 6/1999 | Schwartz | 6,338,727 | B1 | 1/2002 | Noda et al. |
| 5,921,982 | A | 7/1999 | Lesh et al. | 6,364,899 | B1 | 4/2002 | Dobak, III |
| 5,938,660 | A | 8/1999 | Swartz et al. | 6,368,304 | B1 | 4/2002 | Aliberto et al. |
| 5,957,917 | A | 9/1999 | Doiron et al. | 6,379,378 | B1 | 4/2002 | Werneth et al. |
| 5,957,963 | A | 9/1999 | Dobak, III | 6,383,151 | B1 | 5/2002 | Diederich et al. |
| 5,964,751 | A | 10/1999 | Amplatz et al. ............. 606/15 | 6,383,180 | B1 | 5/2002 | Lalonde et al. |
| 5,967,976 | A | 10/1999 | Larsen et al. ............... 606/374 | 6,383,210 | B1 | 5/2002 | Magers et al. |
| 5,968,009 | A | 10/1999 | Simán | 6,391,224 | B1 | 5/2002 | Wowk |
| 5,971,979 | A | 10/1999 | Joye et al. | 6,393,320 | B2 | 5/2002 | Lasersohn et al. |
| 5,971,983 | A | 10/1999 | Lesh | 6,405,080 | B1 | 6/2002 | Lasersohn et al. |
| 5,989,238 | A | 11/1999 | Ginsburg | 6,409,747 | B1 | 6/2002 | Gobin et al. |
| 6,004,289 | A | 12/1999 | Saab | 6,416,511 | B1 | 7/2002 | Lesh et al. |
| 6,007,692 | A | 12/1999 | Herbert et al. | 6,416,533 | B1 | 7/2002 | Gobin et al. |
| 6,011,995 | A | 1/2000 | Guglielmi et al. | 6,419,643 | B1 | 7/2002 | Shimada |
| 6,012,457 | A | 1/2000 | Lesh | 6,428,563 | B1 | 8/2002 | Keller |
| 6,019,783 | A | 2/2000 | Philips et al. | 6,432,124 | B1 | 8/2002 | Worthen et al. |
| 6,022,336 | A | 2/2000 | Zadno-Azizi et al. | 6,497,721 | B2 | 12/2002 | Ginsburg et al. ............ 606/106 |
| 6,024,740 | A | 2/2000 | Lesh et al. | 6,652,515 | B1 | 11/2003 | Maguire et al. ............. 606/41 |
| 6,033,383 | A | 3/2000 | Ginsburg | 2001/0001830 | A1 | 5/2001 | Dobak, III et al. |
| 6,042,559 | A | 3/2000 | Dobak, III | 2001/0001831 | A1 | 5/2001 | Dobak, III et al. |
| 6,051,019 | A | 4/2000 | Dobak, III | 2001/0001832 | A1 | 5/2001 | Dobak, III et al. |
| 6,063,101 | A | 5/2000 | Jacobsen et al. ............. 606/1.11 | 2001/0002442 | A1 | 5/2001 | Dobak, III |
| 6,096,068 | A | 8/2000 | Dobak, III et al. | 2001/0005791 | A1 | 6/2001 | Ginsburg et al. |
| 6,106,518 | A | 8/2000 | Wittenberger et al. | 2001/0007927 | A1 | 7/2001 | Koblish et al. |
| 6,110,168 | A | 8/2000 | Ginsburg | 2001/0007951 | A1 | 7/2001 | Dobak, III |
| 6,117,101 | A | 9/2000 | Diederich et al. | 2001/0008975 | A1 | 7/2001 | Dobak, III et al. |
| 6,126,684 | A | 10/2000 | Gobin et al. | 2001/0010011 | A1 | 7/2001 | Aliberto et al. |
| 6,146,411 | A | 11/2000 | Noda et al. | 2001/0011184 | A1 | 8/2001 | Dobak, III et al. |
| 6,146,814 | A | 11/2000 | Millet | 2001/0011185 | A1 | 8/2001 | Dobak, III et al. |
| 6,149,670 | A | 11/2000 | Worthen et al. | 2001/0014802 | A1 | 8/2001 | Tu |
| 6,149,673 | A | 11/2000 | Ginsburg | 2001/0016763 | A1 | 8/2001 | Lasheras et al. |
| 6,149,676 | A | 11/2000 | Ginsburg | 2001/0016764 | A1 | 8/2001 | Dobak, III |
| 6,149,677 | A | 11/2000 | Dobak, III | 2001/0021865 | A1 | 9/2001 | Dobak, III et al. |
| 6,152,144 | A | 11/2000 | Lesh et al. | 2001/0021866 | A1 | 9/2001 | Dobak, III et al. |
| 6,164,283 | A | 12/2000 | Lesh | 2001/0027333 | A1 | 10/2001 | Schwartz |
| 6,165,207 | A | 12/2000 | Balding et al. | 2001/0029394 | A1 | 10/2001 | Dobak, III et al. |
| 6,168,594 | B1 | 1/2001 | LaFontaine et al. | 2001/0031946 | A1 | 10/2001 | Walker et al. |
| 6,182,666 | B1 | 2/2001 | Dobak, III | 2001/0032003 | A1 | 10/2001 | Pecor |
| 6,193,644 | B1 | 2/2001 | Dobak, III et al. | 2001/0032004 | A1 | 10/2001 | Werneth |
| 6,206,004 | B1 | 3/2001 | Schmidt et al. | 2001/0039440 | A1 | 11/2001 | Lasheras et al. |
| 6,213,126 | B1 | 4/2001 | LaFontaine et al. | 2001/0041923 | A1 | 11/2001 | Dobak, III |
| 6,217,528 | B1 | 4/2001 | Koblish et al. | 2001/0044644 | A1 | 11/2001 | Keller et al. |
| 6,224,624 | B1 | 5/2001 | Lasheras et al. | 2001/0047191 | A1 | 11/2001 | Lasersohn et al. |
| 6,231,561 | B1 | 5/2001 | Frazier et al. | 2001/0047192 | A1 | 11/2001 | Lasersohn et al. |
| 6,231,594 | B1 | 5/2001 | Dae | 2001/0047196 | A1 | 11/2001 | Ginsburg et al. |
| 6,231,595 | B1 | 5/2001 | Dobak, III | 2001/0049545 | A1 | 12/2001 | Lasersohn et al. |
| 6,235,018 | B1 | 5/2001 | Lepivert | 2002/0002394 | A1 | 1/2002 | Dobak, III |
| 6,235,019 | B1 | 5/2001 | Lehmann et al. | 2002/0004675 | A1 | 1/2002 | Lasheras |
| 6,235,048 | B1 | 5/2001 | Dobak, III | 2002/0007179 | A1 | 1/2002 | Dobak, III et al. |
| 6,238,428 | B1 | 5/2001 | Werneth et al. | 2002/0007202 | A1 | 1/2002 | Dobak, III et al. |
| 6,241,718 | B1 | 6/2001 | Arless et al. | 2002/0007203 | A1 | 1/2002 | Gilmartin et al. |

| | | | |
|---|---|---|---|
| 2002/0016621 A1 | 2/2002 | Werneth et al. | |
| 2002/0022823 A1 | 2/2002 | Luo et al. | |
| 2002/0026227 A1 | 2/2002 | Philips | |
| 2002/0029016 A1 | 3/2002 | Pham et al. | |
| 2002/0032430 A1 | 3/2002 | Luo et al. | |
| 2002/0032438 A1 | 3/2002 | Lafontaine | |
| 2002/0032474 A1 | 3/2002 | Dobak, III et al. | |
| 2002/0040717 A1 | 4/2002 | Dobak, III | |
| 2002/0045892 A1 | 4/2002 | Kramer | |
| 2002/0045925 A1 | 4/2002 | Keller et al. | |
| 2002/0049409 A1 | 4/2002 | Noda et al. | |
| 2002/0049410 A1 | 4/2002 | Noda et al. | |
| 2002/0049484 A1 | 4/2002 | Werneth et al. | |
| 2002/0066458 A1 | 6/2002 | Aliberto et al. | |
| 2002/0068964 A1 | 6/2002 | Dobak, III | |
| 2002/0077665 A1 | 6/2002 | Kordis et al. | |
| 2002/0077680 A1 | 6/2002 | Noda | |
| 2002/0082671 A1 | 6/2002 | Magers et al. | |
| 2002/0091378 A1 | 7/2002 | Dobak, III et al. | |
| 2002/0091429 A1 | 7/2002 | Dobak, III et al. | |
| 2002/0091430 A1 | 7/2002 | Dobak, III et al. | |
| 2002/0095200 A1 | 7/2002 | Dobak, III et al. | |
| 2002/0095201 A1 | 7/2002 | Worthen et al. | |
| 2002/0099364 A1 | 7/2002 | LaLonde | |
| 2002/0099427 A1 | 7/2002 | Dobak, III | |
| 2002/0103519 A1 | 8/2002 | Dobak, III et al. | |
| 2002/0111616 A1 | 8/2002 | Dea et al. | |
| 2002/0111657 A1 | 8/2002 | Dae et al. | |
| 2002/0115995 A1 | 8/2002 | Lesh et al. | 606/41 |
| 2002/0156469 A1 | 10/2002 | Yon et al. | 606/21 |

FOREIGN PATENT DOCUMENTS

| | | |
|---|---|---|
| AU | 685559 B2 | 1/1998 |
| AU | 743945 B2 | 8/1998 |
| AU | 737433 B2 | 2/1999 |
| AU | 739996 B2 | 8/1999 |
| AU | 734506 C | 10/1999 |
| CA | 2177982 A | 6/1995 |
| CN | 1082382 A | 2/1994 |
| EP | 0655225 A1 | 5/1993 |
| EP | 0 664 990 | 11/1997 |
| EP | 1205167 A2 | 5/2002 |
| FR | 2 447 406 | 3/1980 |
| SU | 806 029 | 2/1981 |
| WO | WO 91/05528 | 5/1991 |
| WO | WO 91/17788 | 11/1991 |
| WO | WO 93/04727 | 3/1993 |
| WO | WO 94/16760 | 8/1994 |
| WO | WO 95/01814 | 1/1995 |
| WO | WO 95/15115 | 6/1995 |
| WO | WO 96/07448 | 3/1996 |
| WO | WO 96/10367 | 4/1996 |
| WO | WO 96/40347 | 12/1996 |
| WO | WO 97/01374 | 1/1997 |
| WO | WO 97/25011 | 7/1997 |
| WO | WO 99/02096 | 1/1998 |
| WO | WO 98/26931 | 6/1998 |
| WO | WO 98/31312 | 7/1998 |
| WO | WO 98/37822 | 9/1998 |
| WO | WO 98/38934 | 9/1998 |
| WO | WO 98/49957 | 11/1998 |
| WO | WO 99/00064 | 1/1999 |
| WO | WO 99/04211 | 1/1999 |
| WO | WO 99/27862 | 6/1999 |
| WO | WO 99/37226 | 7/1999 |
| WO | WO 99/37726 | 7/1999 |
| WO | WO 99/48449 | 9/1999 |
| WO | WO 99/44519 | 10/1999 |
| WO | WO 99/52455 | 10/1999 |
| WO | WO 99/56812 | 11/1999 |
| WO | WO 99/66970 | 12/1999 |
| WO | WO 99/66971 | 12/1999 |
| WO | WO 00/09054 | 2/2000 |
| WO | WO 00/10494 | 3/2000 |
| WO | WO 00/32126 | 6/2000 |
| WO | WO 00/38601 | 7/2000 |
| WO | WO 00/42931 | 7/2000 |
| WO | WO 00/42932 | 7/2000 |
| WO | WO 00/42933 | 7/2000 |
| WO | WO 00/47145 | 8/2000 |
| WO | WO 00/48670 | 8/2000 |
| WO | WO 00/48760 | 8/2000 |
| WO | WO 00/51511 | 9/2000 |
| WO | WO 00/51534 | 9/2000 |
| WO | WO 00/51683 | 9/2000 |
| WO | WO 00/53135 | 9/2000 |
| WO | WO 00/56237 | 9/2000 |
| WO | WO 00/57823 | 10/2000 |
| WO | WO 00/59390 | 10/2000 |
| WO | WO 00/62837 | 10/2000 |
| WO | WO 00/66053 | 11/2000 |
| WO | WO 00/67648 | 11/2000 |
| WO | WO 00/67656 | 11/2000 |
| WO | WO 00/67830 | 11/2000 |
| WO | WO 00/67832 | 11/2000 |
| WO | WO 00/72779 | 12/2000 |
| WO | WO 00/72787 | 12/2000 |
| WO | WO 00/76570 | 12/2000 |
| WO | WO 01/03606 | 1/2001 |
| WO | WO 01/08580 | 2/2001 |
| WO | WO 01/10323 | 2/2001 |
| WO | WO 01/10365 | 2/2001 |
| WO | WO 01/12061 | 2/2001 |
| WO | WO 01/12122 | 2/2001 |
| WO | WO 01/13809 | 3/2001 |
| WO | WO 01/13837 | 3/2001 |
| WO | WO 01/17471 | 3/2001 |
| WO | WO 01/19447 | 3/2001 |
| WO | WO 01/26590 | 4/2001 |
| WO | WO 01/30413 | 5/2001 |
| WO | WO 01/34225 | 5/2001 |
| WO | WO 01/37919 | 5/2001 |
| WO | WO 01/41664 | 6/2001 |
| WO | WO 01/41708 | 6/2001 |
| WO | WO 01/43661 | 6/2001 |
| WO | WO 01/49236 | 7/2001 |
| WO | WO 01/52781 | 7/2001 |
| WO | WO 01/54618 | 8/2001 |
| WO | WO 01/54764 | 8/2001 |
| WO | WO 01/56517 | 8/2001 |
| WO | WO 01/58397 | 8/2001 |
| WO | WO 01/64145 | 9/2001 |
| WO | WO 01/64146 | 9/2001 |
| WO | WO 01/66052 | 9/2001 |
| WO | WO 01/74276 | 10/2001 |
| WO | WO 01/76655 | 10/2001 |
| WO | WO 01/78580 | 10/2001 |
| WO | WO 01/87379 | 11/2001 |
| WO | WO 01/95840 | 12/2001 |
| WO | WO 02/07793 | 1/2002 |
| WO | WO 02/26175 | 4/2002 |
| WO | WO 02/26176 | 4/2002 |
| WO | WO 02/26285 | 4/2002 |
| WO | WO 02/26307 | 4/2002 |
| WO | WO 02/28300 | 4/2002 |
| WO | WO 02/36180 | 5/2002 |
| WO | WO 02/38091 | 5/2002 |
| WO | WO 02/43577 | 6/2002 |
| WO | WO 02/47577 | 6/2002 |
| WO | WO 02/47742 | 6/2002 |
| WO | WO 02/055129 | 7/2002 |
| WO | WO 02/056938 | 7/2002 |
| WO | WO 02/058606 | 8/2002 |
| WO | WO 02/060514 | 8/2002 |

OTHER PUBLICATIONS

Ambrus; *The Biphasic Nature and Temperature Dependence of the Activation of Human Plasminogen by Urokinase*; May 1979; pp. 339-347; Research Communications in Chemical Pathology and Pharmacology, vol. 24, No. 2.

Arless, S. G., *CryoCath Completes a Third Round Private Placement for CDN$10 Million*, Apr. 7, 1999, Kirkland, Quebec, Press Release.

Arless, S. G., *CryoCath Technologies, Inc.*, Oct. 1999, press release.

Asbach, H. W. et al, *The Effects of Extreme Cold on Major Blood Vessels; An Experimental Study* (abs.), Urologe A., May 1975, vol. 14, No. 3, pp. 150-153.

Atrionix (Palo Alto, CA), *AF Ablation and Monitoring*, http://www.medicaldata.com/members/MPM/3-2000/0300-3.asp, Apr. 19, 2000.

Bigelo; *Hypothermia, Its Possible Role in Cardiac Surgery*; Nov. 1959; pp. 849-866; Annals of Surgery, vol. 132, No. 5.

Bokeriia, A. A. et al., *Cryogenic Effect on the coronary Arteries in Animal Experiments* (abs.), Biull. Eksp.Biol. Med., Jun. 1988, vol. 105, Nov. 6, pp. 741-743.

Cheatle; *Cryostripping the Long and Short Saphenous Veins*; Jan. 1993; one page; Br. J. Surg., vol. 80.

CryoCath Technologies, Inc., *Affairs of the Heart*, The Gazette, Montreal, Feb. 16,1998.

Dexter, *Blood Warms as It Flows Retrograde from a Femoral Cannulation Site to the Carotid Artery During Cardiopulmonary Bypass*; Nov. 1994; pp. 393-397; Perfusion, vol. 9, No. 6.

Dorval, J-F et al. *Induction of Extracellular Matrix Expression in the Arterial Wall after the Application of Cryotherapy in a Porcine PTCA Model*, ACC Meeting, Mar. 2000, No. 1131-116.

Dubuc, M. et al. *Catheter Cryoablation: A Novel Technology for Ablation of Cardiac Arrhythmias*, presented at AHA, Nov. 1996.

Dubuc, M. et al. *Feasibility of Cardiac Cryoablation Using a Transvenous Steerable Electrode Catheter*, reprint Journal of Interventional Electrophysiology, vol. 2, No. 3, Kluwer Academic Publishers, 1998, vol. 2, pp. 285-292.

Dubuc, M. et al. *Reversible Electrophysiologic Effects Using Ice Mapping with a Cryoablation Catheter*, Montreal, Quebec, Canada, Brigham and Women's Hospital, Boston, MA, presented at NSPE, May 1997.

Dubuc, M. et al. *Transvenous Catheter Ice Mapping and Cryoablation of the Atrioventricular Node in Dogs*, Oct. 1999, P.A.C.E., vol. 22, No. 10, pp. 1488-1498.

Ducharme, A. et al. *Intracardiac Echocardiography Monitoring of Catheter Cryoablation*, presented at AHA, Nov. 1998.

Gillinov; *Superior Cerebral Protection with Profound Hypothermia During Circulatory Arrest*; Nov. 1992; pp. 1432-1439; Ann. Thorac. Surg., vol. 55.

Haines, N. S., *Biophysics and Pathology of Catheter Energy Delivery Systems* (abs.), Prog. Cardiovasc. Dis., Jan.-Feb. 1995, vol. 37, No. 4, pp. 185-204.

Higazi; *The Effect of Ultrasonic Irradiation and Temperature on Fibrinolytic Activity in Vitro*; Aug. 1992; p. 251-253; Thrombosis Research, vol. 69, No. 2.

Imamaki; *Retrograde Cerebral Perfusion with Hypothermic Blood Provides Efficient Protection of the Brain*; Jul. 1995; pp. 325-333; Journal of Cardiac Surgery, vol. 10, No. 4, Part 1.

Jolin; *Management of a Giant Intracranial Aneurysm Using Surface-Heparinized Extracorporeal Circulation and Controlled Deep Hypothermic Low Flow Perfusion*; Aug. 1992; pp. 756-760; Acta Anaesthesiologica Scandinavia.

Jos, R.C. Jansen, Ph.D., et al. (1997) *Near Continuous Cardiac Output by Thermodilution*. Journal of Clinical Monitoring 13:233-239.

Keane, D. et al. *Percutaneous Cryothermal Catheter Ablation for the Creation of Linear Atrial Lesions*, Massachusetts General Hospital, Boston, MA, presented at NASPE, May 1999.

Kimoto; *Open Heart Surgery under Direct Vision with the Aid of Brain-Cooling by Irrigation*; Jul. 1955; pp. 592-603; Surgery, vol. 39, No. 4.

Ladd, A. P. et al. *Cryosurgical Effects on Growing Vessels* (abs.), Am Surg. Jul. 1999, vol. 65, No. 7, pp. 677-682.

Lustgarten, D. L et al. (1999), *Cryothermal Ablation: Mechanism of Tissue Injury and Current Experience in the Treatment of Tachyarrhythmias*, 47(6):481-498.

Marekovic, Z.; *Abstract of Renal Hypothermia in Situ by Venous Passages: Experimental Work on Dogs*; 1980; Eur Urol 6(2); 1 page.

Marsland, A. R. et al., *Cryogenic Damage to Peripheral Nerves and Blood Vessels in the Rat*, Br. J. Anaesth., Jun. 1983, vol. 55, No. 6, pp. 555-558.

Meden; *Effect of Hypothermia and Delayed Thrombolysis in a Rat Embolic Stroke Model*; Dec. 1993; pp. 91-98; Acta Neurologica Scandinavica.

Meden; *The Influence of Body Temperature on Infarct Volume and Thrombolytic Therapy in a Rat Embolic Stroke Model*; Feb. 1994; pp. 131-138; Brain Research, vol. 647.

Milleret; Abstract of *Cryosclerosis of the Saphenous Veins in Varicose Reflux in the Obese and Elderly*; 10.1981; one page; Phlebologie, vol. 34, No. 4.

Parkins; *Brain Cooling in the Prevention of Brain Damage During Periods of Circulatory Occlusion in Dogs*; Apr. 1954; pp. 284-289; Annals of Surgery, vol. 140, No. 3.

Pham, I. et al., *Adenovirus Mediated Atrial Natriuretic Peptide Gene Transfer in Rat Pulmonary Vascular Smooth Muscle Cells Leads to Inhibition of Cell Growth and Apoptosis*, Section on: Therapeutic Strategies in Vascular Remodeling, AHA Meeting, Nov. 1998, Dallas, Texas, No. 3544.

Piepgras; *Rapid Active Internal Core Cooling for Induction of Moderate Hypothermia in Head Injury by Use of an Extracorporeal Heat Exchanger*, Feb. 1998; pp. 311-318; Neurosurgery. vol. 42, No. 2.

Plattner, O. et al. *Efficacy of Intraoperative Cooling Methods*, 1997, Anesthesiology, November, vol. 87, No. 5, pp. 1089-1095.

Rijken; *Plasminogen Activation at Low Temperatures in Plasma Samples Containing Therapeutic Concentrations of Tissue-Type Plasminogen Activator or Other Thrombolytic Agents*; Oct. 1989; pp. 47-52; place of publication unknown.

Schwartz, A. E. et al.; (1996); *Isolated cerebral hypothermia by single carotid artery perfusion of extracorporeally cooled blood in baboons*; Neurosurgery 39(3):577-582.

Schwartz; *Cerebral Blood Flow during Low-flow Hypothermic Cardiopulmonary Bypass in Baboons*; Jun. 1994; pp. 959-964; Anesthesiology, vol. 81, No. 4.

Schwartz; *Selective Cerebral Hypothermia by Means of Transfemoral Internal Carotid Artery Catheterization*; May 1996; pp. 571-572; Radiology, vol. 201, No. 2.

Steen; *The Detrimental Effects of Prolonged Hypothermia and Rewarming in the Dog*; Aug. 1979 ;pp. 224-230; Anesthesiology, vol. 52, No. 3.

Tanguay, J.-F., *A New Cryotherapy Catheter to Prevent Restenosis* (abs.), 11th Transcatheter Cardiovascular Therapeutics, Sep. 1999.

Tanguay, J-F et al. *A New Cryocatheter Treatment Improves Vascular Remodeling after Angioplasty*, presented at AHA, Nov. 1998.

Tanguay, J-F et al., *A New Cryocatheter Treatment Improves Vascular Remodeling after Angioplasty*, Section on Therapeutic Strategies in Vascular Remodeling, AHA Meeting, Nov. 1998, Dallas, Texas, No. 3543.

Vandam; *Hypothermia*; Sep. 1959; pp. 546-553; The New England Journal of Medicine.

White; *Cerebral Hypothermia and Circulatory Arrest*; Jul. 1978; pp. 450-458; Mayo Clinic Proceedings, vol. 53.

Yenari; *Thrombolysis with Tissue Plasminogen Activator (TPA) is Temperature Dependent*; Jul. 1994; pp. 475-481; Thrombosis Research, vol. 77, No. 5.

Yoshihara; *Changes in Coagulation and Fibrinolysis Occurring in Dogs during Hypothermia*; Aug. 1984; pp. 503-512; Thrombosis Research, vol. 37, No. 4.

Zarins; *Circulation in Profound Hypothermia*; Nov. 1972; pp. 97-104; Journal of Surgical Research, vol. 14, No. 2.

Thibault, B., C. Villemaire, M. Talajic, D. Roy, S. Nattel, T. Ki Leung, M. Dubuc, "Catheter Cryoablation is a More Effective and Potentially Safer Method to Create Atrial Conduction Block: Comparison with Radiofrequency Ablation," *NASPE Abstracts*, Apr. 1998, Part II, PACE, V. 21(620):944.

Colvett, K. T. et al. "Opportunities with Combined Modality Therapy for Selective Organ Preservation in Muscle-Invasive Bladder Cancer," May 1996, *Journ. Surg. Oncology* 63:202-201.

Hayes et al. "Temperature Control in extracorporeal cirulation," *Aug. 17, 1968, Brit. Med. J.* 2(615):430.

Mass, C. et al. "Intermittent Antegrade/Selective Cerebral Perfusion during Circulatory Arrest for Repair of the Aortic Arch," 1997, *Perfusion*, 12:127-132.

\* cited by examiner

METHOD AND DEVICE FOR PERFORMING COOLING-OR CRYO-THERAPIES FOR, E.G., ANGIOPLASTY WITH REDUCED RESTENOSIS OR PULMONARY VEIN CELL NECROSIS TO INHIBIT ATRIAL FIBRILLATION

CROSS-REFERENCE TO RELATED APPLICATIONS

This application is a continuation of U.S. patent application Ser. No. 10/039,466, filed Jan. 3, 2002 entitled "Method and Device for Performing Cooling- or Cryo-Therapies for, e.g., Angioplasty with Reduced Restenosis or Pulmonary Vein Cell Necrosis to Inhibit Atrial Fibrillation", now U.S. Pat. 7,291,144, which is a divisional of U.S. patent application Ser. No. 09/516,319, filed Mar. 1, 2000, entitled "Method and Device for Performing Cooling- or Cryo-Therapies for, e.g., Angioplasty with Reduced Restenosis or Pulmonary Vein Cell Necrosis to Inhibit Atrial Fibrillation", now abandoned, which is a continuation-in-part of U.S. patent application Ser. No. 09/052,545, filed Mar. 31, 1998, entitled "Circulating Fluid Hypothermia Method and Apparatus", now U.S. Pat. No. 6,231,595, and a continuation-in-part of U.S. patent application Ser. No. 09/215,038, filed Dec. 16, 1998, entitled "Inflatable Catheter for Selective Organ Heating and Cooling and Method of Using the Same", now U.S. Pat. No. 6,261,312.

CROSS-REFERENCE TO MICROFICHE APPENDIX (none)

BACKGROUND OF THE INVENTION

Balloon angioplasty, or the technology of reshaping of a blood vessel for the purpose of establishing vessel patency using a balloon tipped catheter, has been known since the late 1970's. The procedure involves the use of a balloon catheter which is guided by means of a guidewire through a guiding catheter to the target lesion or vessel blockage. The balloon typically is equipped with one or more marker bands that allows the interventionalist to visualize the position of the balloon in reference to the lesion with the aid of fluoroscopy. Once in place, i.e., centered with the lesion, the balloon is inflated with a biocompatible fluid, and pressurized to the appropriate pressure to allow the vessel to open.

Typical procedures are completed with balloon inflation pressures between 8 and 12 atmospheres. A percentage of lesions, typically heavily calcified lesions, require much higher balloon inflation pressures, e.g., upward of 20 atmospheres. At times, the balloon inflation procedure is repeated several times before the lesion or blockage will yield. The placement of stents after angioplasty has become popular as it reduces the rate of restenosis.

Restenosis refers to the renarrowing of the vascular lumen following vascular intervention such as a balloon angioplasty procedure or stent insertion. Restenosis is clinically defined as a greater than 50% loss of initial lumen diameter. The mechanism or root causes of restenosis are still not fully understood. The causes are multifactoral, and are partly the result of the injury caused by the balloon angioplasty procedure and stent placement. With the advent of stents, restenosis rates have dropped from over 30% to 10-20%. Recently, the use and effectiveness of low-dose radiation administered intravascularly following angioplasty is being evaluated as a method to alter the DNA or RNA of an affected vessel's cells in the hope of reducing cell proliferation.

Besides restenosis, another cardiological malady is atrial fibrillation. Atrial fibrillation refers to very rapid irregular contractions of the atria of the heart resulting in a lack of synchronization between the heartbeat and the pulse. The irregular contractions are due to irregular electrical activity that originates in the area of the pulmonary veins. A proposed device, currently under development, for treating atrial fibrillation is a balloon filled with saline that can be ultrasonically agitated and heated. This device is inserted in the femoral vein and snaked into the right atrium. The device is then poked through the interatrial septum and into the left atrium, where it is then angled into the volume adjoining the suspect pulmonary vein with the left atrium.

Research in atrial fibrillation indicates that substantially complete circumferential necrosis is required for a therapeutic benefit. The above technique is disadvantageous in that circumferential portions of the tissue, desired to be necrosed, are not in fact affected. Other techniques, including RF ablation, are similarly inefficient. Moreover, these techniques leave the necrosed portions with jagged edges, i.e., there is poor demarcation between the healthy and the necrosed tissue. These edges can then cause electrical short circuits, and associated electrical irregularities, due to the high electric fields associated with jagged edges of a conductive medium.

The above technique is also disadvantageous in that heating is employed. Heating is associated with several problems, including increased coagulum and thrombus formation, leading to emboli. Heating also stimulates stenosis of the vein. Finally, since tissues can only safely be heated to temperatures of less than or about 75° C.-85° C. due to charring and tissue rupture secondary to steam formation. The thermal gradient thus induced is fairly minimal, leading to a limited heat transfer. Moreover, since heating causes tissues to become less adherent to the adjacent heat transfer element, the tissue contact with the heat transfer element is also reduced, further decreasing the heat transfer.

SUMMARY OF THE INVENTION

The present invention provides an enhanced method and device to inhibit or reduce the rate of restenosis following angioplasty or stent placement. The invention is similar to placing an ice pack on a sore or overstrained muscle for a period of time to minimize or inhibit the bio-chemical events responsible for an associated inflammatory response. An embodiment of the invention generally involves placing a balloon-tipped catheter in the area treated or opened through balloon angioplasty immediately following angioplasty. A so-called "cryoplasty" balloon, which can have a dual balloon structure, may be delivered through a guiding catheter and over a guidewire already in place from a balloon angioplasty. The dual balloon structure has benefits described below and also allows for a more robust design, providing significant safety advantages to the patient because two balloons must be broken if cooling fluid is to deleteriously infuse into the patient.

The dual balloon may be centered in the recently opened vessel with the aid of radio opaque marker bands, indicating the "working length" of the balloon. In choosing a working length, it is important to note that typical lesions may have a size on the order of 2-3 cm. A biocompatible heat transfer fluid, which may contain contrast media, may be infused through the space between the dual balloons. While this fluid does not circulate in this embodiment, once it is chilled or even frozen by thermal contact with a cooling fluid, it will stay sufficiently cold for therapeutic purposes. Subsequently, a biocompatible cooling fluid with a temperature between about, e.g., −40° C. and −60° C., may be injected into the interior of the inner balloon, and circulated through a supply lumen and a return lumen. The fluid exits the supply lumen through a skive in the lumen, and returns to the refrigeration unit via another skive and the return lumen.

The biocompatible cooling fluid chills the biocompatible heat transfer fluid between the dual balloons to a therapeutic temperature between about, e.g., 0° C. and −50° C. The chilled heat transfer fluid between the dual balloons transfers thermal energy through the balloon wall and into the adjacent intimal vascular tissue for the appropriate therapeutic length of time. Upon completion of the therapy, the circulation of the biocompatible cooling fluid is stopped, and the heat transfer fluid between the dual balloons withdrawn through the annular space. Both balloons may be collapsed by means of causing a soft vacuum in the lumens. Once collapsed, the cryoplasty catheter may be withdrawn from the treated site and patient through the guiding catheter.

In more detail, in one aspect, the invention is directed to a device to treat tissue, including an outer tube, an inner tube disposed at least partially within the outer tube, and a dual balloon including an inner balloon and an outer balloon, the inner balloon coupled to the inner tube at a proximal and at a distal end, the outer balloon coupled to the inner tube at a distal end and to the outer tube at a proximal end. A first interior volume is defined between the outer balloon and the inner balloon in fluid communication with an inlet in the volume between the outer tube and the inner tube.

Variations of the invention may include one or more of the following. The inner tube may further define a guidewire lumen, a supply lumen, and return lumen. The supply lumen may define a hole or skive such that a fluid flowing in the supply lumen may be caused to flow into a volume defined by the inner balloon, and the return lumen may define a hole or skive such that a fluid flowing in a volume defined by the inner balloon may be caused to flow into the return lumen. The guidewire lumen may extend from a proximal end of the inner tube to a distal end of the inner tube. The device may further comprise at least two radially extending tabs disposed around a circumference of the inner tube to substantially center the inner tube within the dual balloon. The device may further comprise at least one marker band disposed on the inner tube to locate a working region of the device at a desired location. The device may further comprise a source of chilled fluid having a supply tube and a return tube, the supply tube coupled in fluid communication to the supply lumen and the return tube coupled in fluid communication to the return lumen. A source of fluid may also be included, the source of fluid coupled in fluid communication to a volume between the inner balloon and the outer balloon. The fluid may be a perfluorocarbon such as Galden fluid. The fluid may also include contrast media.

In another aspect, the invention is directed to a method of reducing restenosis after angioplasty in a blood vessel. The method includes inserting a catheter into a blood vessel, the catheter having a balloon. The balloon is then inflated with a perfluorocarbon such that an exterior surface of the balloon is in contact with at least a partial inner perimeter of the blood vessel, the perfluorocarbon having a temperature in the range of about −10° C. to −50° C.

Variations of the method may include one or more of the following. The method may include disposing the catheter at a desired location using at least one radio opaque marker band. The method may include flowing the perfluorocarbon into the balloon using a supply lumen and exhausting the perfluorocarbon from the balloon using a return lumen. The balloon may be a dual balloon, and the method may further include providing a heat transfer fluid in the volume between the dual balloons. The heat transfer fluid may include a contrast media fluid. The method may include disposing the catheter such that at least a portion of the balloon is in a coronary artery or in a carotid artery.

In yet another aspect, the invention is directed to a method of reducing atrial fibrillation. The method includes inserting a catheter at least partially into the heart, the catheter having a balloon, a portion of the balloon located in the left atrium and a portion of the balloon located in a pulmonary vein. The balloon is then inflated with a perfluorocarbon such that an exterior surface of the balloon is in contact with at least a partial circumference of the portion of the pulmonary vein adjacent the left atrium, the perfluorocarbon having a temperature in the range of about −10° C. to −50° C.

Variations of the method may include one or more of the following. The balloon may have a working region having a length of between about 5 mm and 10 mm. The method may further include inserting a wire having a needle point from the femoral vein into the right atrium and forming a hole using the needle point in the interatrial septum between the right atrium and the left atrium. A guide catheter may then be inserted into the right atrium. A guide wire may further be inserted through the guide catheter into the right atrium and further into a pulmonary vein. The catheter may then be disposed over the guidewire into a volume defined by the joint of the right atrium and the pulmonary vein.

Advantages of the invention may include one or more of the following. The invention inhibits or reduces the rate of restenosis following a balloon angioplasty or any other type of vascular intervention. At least the following portions of the vascular anatomy can benefit from such a procedure: the abdominal aorta (following a stent or graft placement), the coronary arteries (following PTCA or rotational artherectomy), the carotid arteries (following an angioplasty or stent placement), as well as the larger peripheral arteries.

When the invention is used to treat atrial fibrillation, the following advantages inure. The cooled tissue is adherent to the heat transfer element, increasing the heat transfer effected. Since very cold temperatures may be employed, the temperature gradient can be quite large, increasing the heat transfer rate.

In both embodiments, heat transfer does not occur primarily or at all by vaporization of a liquid, thus eliminating a potential cause of bubbles in the body. Nor does cooling occur primarily or at all by a pressure change across a restriction or orifice, this simplifying the structure of the device. Thrombus formation and charring, associated with prior techniques, are minimized or eliminated.

Additional advantages will be apparent from the description that follows, including the drawings and claims.

DETAILED DESCRIPTION

Figure 1A:
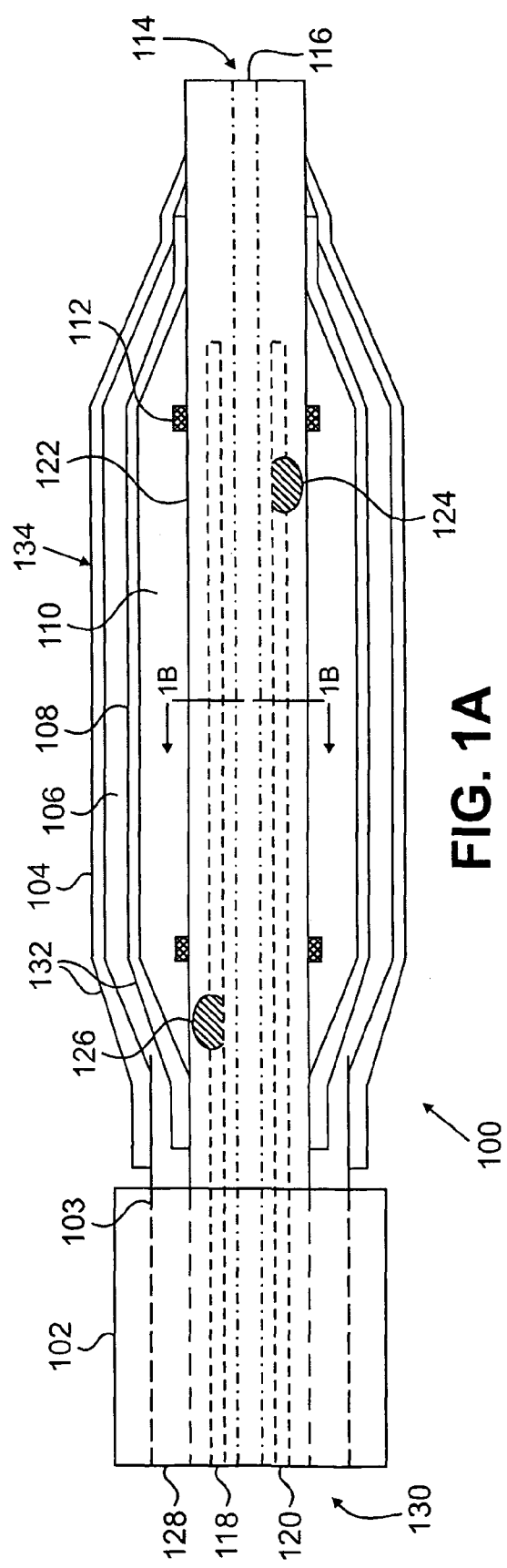
FIG. 1A shows a side schematic view of a catheter according to a first embodiment of the invention.

Referring to FIG. 1A, a catheter 100 is shown according to a first embodiment of the invention. The catheter 100 has a proximal end 130 and a distal end 114. Of course, this figure is not necessarily to scale and in general use the proximal end 130 is far upstream of the features shown in FIG. 1A.

The catheter 100 may be used within a guide catheter 102, and generally includes an outer tube 103, a dual balloon 134, and an inner tube 122. These parts will be discussed in turn.

The guide catheter 102 provides a tool to dispose the catheter 100 adjacent the desired location for, e.g., angioplasty or reduction of atrial fibrillation. Typical guide catheter diameters may be about 6 french to 9 french, and the same may be made of polyether blockamide, polyamides, polyurethanes, and other similar materials. The distal end of the guide catheter is generally adjacent the proximal end of the dual balloon 134, and further is generally adjacent the distal end of the outer tube 103.

The ability to place the guide catheter is a significant factor in the size of the device. For example, to perform angioplasty in the carotid arteries, which have an inner diameter of about 4 to 6 mm, a suitably sized guide catheter must be used. This restricts the size of the catheter 100 that may be disposed within the guide catheter. A typical diameter of the catheter 100 may then be about 7 french or less or about 65 to 91 mils. In a second embodiment described below, a catheter for use in the coronary arteries is described. Of course, which catheter is used in which artery is a matter to be determined by the physician, taking into account such factors as the size of the individual patient's affected arteries, etc.

The outer tube 103 houses the catheter 100 while the latter traverses the length of the guide catheter 102. The outer tube 103 may have a diameter of about 4 french to 7 french, and the same may be made of polyether blockamide, poly-butylene terephalate, polyurethane, polyamide, polyacetal polysulfone, polyethylene, ethylene tetrafluoroethylene, and other similar materials.

The distal end of the outer tube 103 adjoins the proximal end of the dual balloon 134. The outer tube 103 provides a convenient location for mounting a proximal end of an outer balloon 104 within the dual balloon 134, and further may provide an inlet 128 for providing a fluid such as a liquid to a first interior volume 106 between the dual balloons. In some cases, an inlet 128 per se may not be necessary: the fluid, which may also be a sub-atmospheric level of gas or air, may be provided during manufacture in the first interior volume 106. In this case, the proximal and distal ends of the first interior volume may be sealed during manufacture. The inlet 128 may be at least partially defined by the annular volume between the interior of the outer tube 103 and the exterior of the inner tube 122.

The dual balloon 134 includes an outer balloon 104 and an inner balloon 108. Between the two is the first interior volume 106. The outer balloon 104 may be inflated by inflating the interior volume 106. The inner balloon 108 has a second interior volume 110 associated with the same. The inner balloon 108 may be inflated by inflating the second interior volume 110.

To avoid the occurrence of bubbles in the bloodstream, both the inner balloon 108 and the outer balloon 104 may be inflated using biocompatible liquids, such as Galden® fluid, perfluorocarbon-based liquids, or various contrast agents. There is no need that the fluid inflating one of the interior volumes be the same fluid as that inflating the other. Additional details on these fluids are described below.

In the case of the first interior volume 106, this fluid may be, e.g., stationary or static: in other words, it need not be circulated. In the case of the second interior volume 110, this fluid would in general be circulated by an external chiller (not shown). The chiller may be, e.g., a gear pump, peristaltic pump, etc. It may be preferable to use a gear pump over a peristaltic pump as the attainable pressure of the former is generally greater than that of the latter. Moreover, gear pumps have the advantageous property of being linear, i.e., their output varies in direction proportion with their revolutions per minute. Two types of gear pumps which may be employed include radial spur gear pumps and helical tooth gear pumps. Of these, the helical tooth gear pump may be more preferable as the same has been associated with higher pressures and a more constant output. The ability to achieve high pressures may be important as the cooling fluid is required to pass through a fairly narrow, e.g., five to seven french, catheter at a certain rate. For the same reason, the viscosity of the fluid, at the low temperatures, should be appropriately low. For example, an appropriate type of fluid may be Galden® fluid, and in particular Galden®g fluid item number "HT-55", available from Ausimont Inc. of Thorofare, N.J. At −55° C., this fluid has a viscosity of 2.1 centiStokes. At −70° C., this fluid has a viscosity of 3.8 centiStokes. It is believed that fluids with such viscosities at these temperatures would be appropriate for use.

The so-called "cones" of the balloons 108 and 104, indicated generally by reference numeral 132, may be made somewhat thicker than the remainder of the balloon sections. In this way, the heat transfer efficiency in these sections is significantly less than over the remainder of the balloon sections, this "remainder" effectively defining a "working region" of the balloon. In this way, the cooling or "cryoplasty" may be efficiently localized to the affected area rather than spread over the length of the balloon.

Figure 1B:
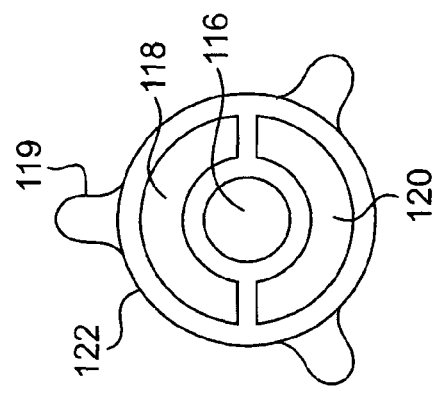
FIG. 1B shows a cross-sectional view of the catheter of FIG. 1A, as indicated by lines 1B-1B in FIG. 1A.

The inner tube 122 is disposed within the interior of the dual balloon 134 and within the interior of the guide catheter 102. The inner tube 122 includes a supply lumen 120, a return lumen 118, and a guidewire lumen 116. The guidewire lumen 116 may have sizes of, e.g., 17 or 21 mils inner diameter, in order to accommodate current standard sized guidewires, such as those having an outer diameter of 14 mils. This structure may be preferable to a coaxial structure, as the pressure drop encountered may be substantially less. In use, the supply lumen 120 may be used to supply a circulating liquid to the second interior volume 110. The return lumen 118 may be used to exhaust the circulating liquid from the second interior volume to the external chiller. As may be seen from FIG. 1A, both lumens 118 and 120 may terminate prior to the distal end 114 of the catheter 100. The lumen arrangement may be seen more clearly in FIG. 1B.

A set of radio opaque marker bands 112 may be disposed on the inner tube 122 at locations substantially adjacent the cones 132 to define a central portion of the "working region" of the balloons 104 and 108. This working region is where the "cryoplasty" procedures described below may substantially occur.

As noted above, the proximal portion of the outer balloon 104 is mounted on the outer tube 103 at its distal end. The distal end of the outer balloon 104 is secured to the distal end of the catheter 100 and along the inner tube 122. In contrast, both the proximal and distal ends of the inner balloon 108 may be secured to the inner tube 122 to create a sealed second interior volume 110.

At least two skives 124 and 126 may be defined by the inner tube 122 and employed to allow the working fluid to exit into the second interior volume 110 and to exhaust the same from the second interior volume 10. As shown in the figure, the skive 124 is in fluid communication with the lumen 120 and the skive 126 is in fluid communication with the lumen 118. Here, "fluid communication" refers to a relationship between two vessels where a fluid pressure may cause a net amount of fluid to flow from one vessel to the other.

The skives may be formed by known techniques. A suitable size for the skives may be from about 50 mils to 125 mils.

A plurality of tabs 119 may be employed to roughly or substantially center the inner tube 122 within the catheter 100. These tabs may have the shape shown, the shape of rectangular or triangular solids, or other such shapes so long as the flow of working fluid is not unduly impeded. In this specification, the phrase "the flow of working fluid is not unduly impeded" is essentially equated to the phrase "substantially center". The tabs 119 may be made of polyether blockamide, poly-butylene terephalate, polyurethane, polyamide, polyacetal polysulfone, polyethylene, ethylene tetrafluoroethylene, and other similar materials, and may have general dimensions of from about 3 mils to 10 mils in height, and by about 10 mils to 20 mils in width.

In a method of use, the guide catheter 102 may be inserted into an affected artery or vein such that the distal tip of the guide catheter is just proximal to an affected area such as a calcified area or lesion. Of course, it is noted that typical lesions do not occur in the venous system, but only in the arterial.

This step provides a coarse estimate of proper positioning, and may include the use of fluoroscopy. The guide catheter may be placed using a guide wire (not shown). Both the guide catheter and guide wire may already be in place as it may be presumed a balloon angioplasty or stent placement has previously been performed.

The catheter 100 may then be inserted over the guide wire via the lumen 116 and through the guide catheter 102. In general, both a guide wire and a guide catheter are not strictly necessary—one or the other may often suffice. During insertion, the dual balloon 134 may be uninflated to maintain a minimum profile. In fact, a slight vacuum may be drawn to further decrease the size of the dual balloon 134 so long as the structural integrity of the dual balloon 134 is not thereby compromised.

When the catheter 100 is distal of the distal tip of the guide catheter 102, a fine positioning step may occur by way of the radio opaque marker bands 112. Using fluoroscopy, the location of the radio opaque marker bands 112 can be identified in relation to the location of the lesion. In particular, the catheter may be advantageously placed at the location of the lesion and further such that the lesion is between the two marker bands. In this way, the working region of the balloon 134 will substantially overlap the affected area, i.e., the area of the lesion.

Once placed, a biocompatible heat transfer fluid, which may also contain contrast media, may be infused into the first interior volume 106 through the inlet 128. While the use of contrast media is not required, its use may allow early detection of a break in the balloon 104 because the contrast media may be seen via fluoroscopy to flow throughout the patient's vasculature. Subsequently a biocompatible cooling fluid may be circulated through the supply lumen 120 and the return lumen 118. Before or during the procedure, the temperature of the biocompatible cooling fluid may be lowered to a therapeutic temperature, e.g., between −40° C. and −60° C., although the exact temperature required depends on the nature of the affected area. The fluid exits the supply lumen 120 through the skive 124 and returns to the chiller through the skive 126 and via the return lumen 118. It is understood that the respective skive functions may also be reversed without departing from the scope of the invention.

The biocompatible cooling fluid in the second interior volume 110 chills the biocompatible heat transfer fluid within the first interior volume 106 to a therapeutic temperature of, e.g., between about −25° C. and −50° C. The chilled heat transfer fluid transfers thermal energy through the wall of the balloon 104 and into the adjacent intimal vascular tissue for an appropriate therapeutic length of time. This time may be, e.g., about ½ to 4 minutes.

Upon completion of the therapy, the circulation of the biocompatible cooling fluid may cease. The heat transfer fluid within the first interior volume 106 may be withdrawn though the inlet 128. The balloons 104 and 108 may be collapsed by pulling a soft vacuum through any or all of the lumens 124, 126, and 128. Following collapse, the catheter 100 may be withdrawn from the treatment site and from the patient through the guide catheter 102.

To inhibit restenosis, the following therapeutic guidelines may be suggested:

|  | Minimum | Average | Maximum |
|---|---|---|---|
| Temperature of heat transfer fluid | −20° C. | −55° C. | −110° C. |
| Temperature achieved at intimal wall | 0° C. to −10° C. | −20° C. to −30° C. | −50° C. to −100° C. |
| Depth of penetration of intema/media | 10ths of mm | 1 mm | 3 mm |
| Length of time fluid is circulating | 30 seconds | 1-2 min | 4-5 min |

Substantially the same catheter may be used to treat atrial fibrillation. In this method, the catheter is inflated as above once it is in location. The location chosen for treatment of atrial fibrillation is such that the working region spans a portion of the left atrium and a portion of the affected pulmonary vein. Thus, in this embodiment, the working region of the catheter may have a length of about 5 mm to 30 mm. The affected pulmonary vein, of the four possible pulmonary veins, which enter the left atrium, may be determined by electrophysiology studies.

To maneuver the catheter into this location, a catheter with a needle point may first be inserted at the femoral vein and routed up to the right atrium. The needle of the catheter may then be poked through the interatrial septum and into the left atrium. The catheter may then be removed if desired and a guide catheter disposed in the same location. A guide wire may be used through the guide catheter and may be maneuvered at least partially into the pulmonary vein. Finally, a catheter such as the catheter 100 may be placed in the volume defining the intersection of the pulmonary vein and the left atrium.

A method of use similar to that disclosed above is then employed to cool at least a portion of, and preferably all of, the circumferential tissue. The coldness of the balloon assists in the adherence of the circumferential tissue to the balloon, this feature serving to increase the overall heat transfer rate.

The catheter 100 above may be particularly useful for procedures in the carotid arteries by virtue of its size. For use in the coronary arteries, which are typically much smaller than the carotid artery, an even smaller catheter may be desired.

Figure 2A:
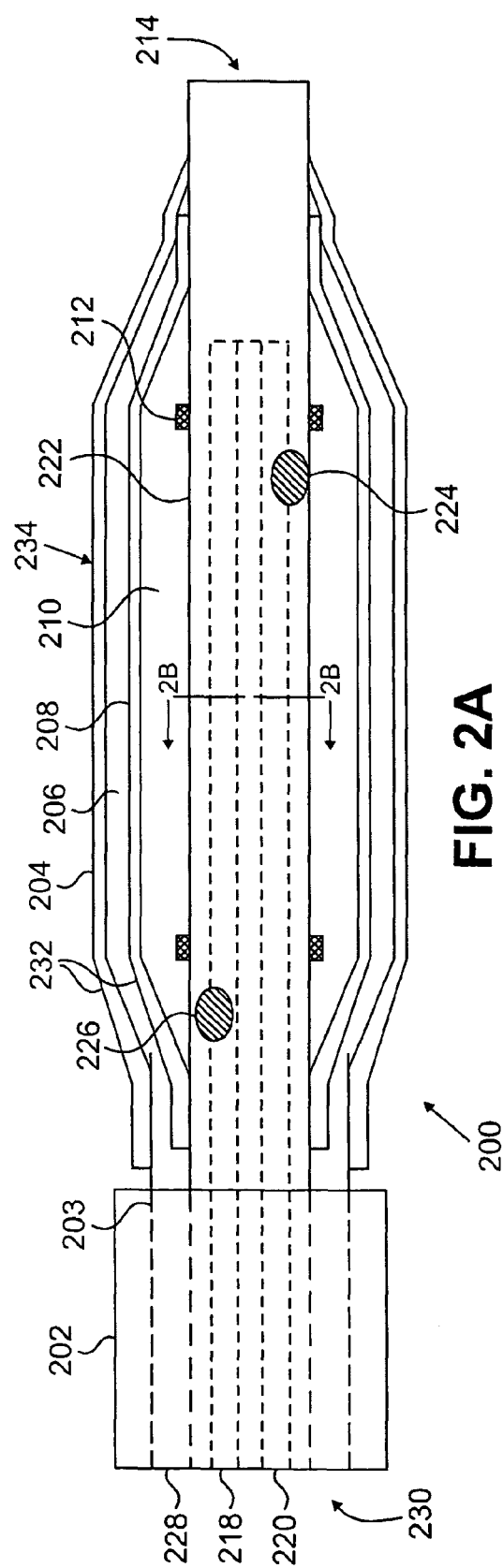
FIG. 2A shows a side schematic view of a catheter according to a second embodiment of the invention.
Figure 2B:
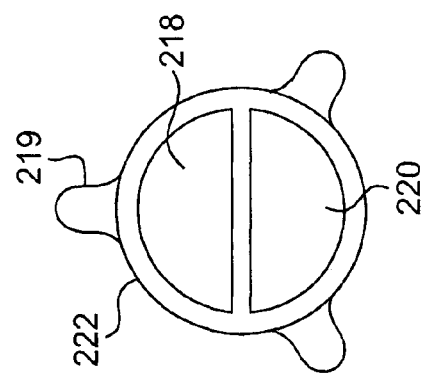
FIG. 2B shows a cross-sectional view of the catheter of FIG. 2A, as indicated by lines 2B-2B in FIG. 2A.

Referring to FIG. 2A, a catheter 200 is shown according to a second embodiment of the invention. This embodiment may be particularly useful for use in the coronary arteries because the dimensions of the catheter 200 may be considerably smaller than the dimensions of the catheter 100. However, in several ways the catheter 200 is similar to the above-described catheter 100. In particular, the catheter 200 has a proximal end 230 and a distal end 214 and may be used within a guide catheter 202. The catheter 200 includes an outer tube 203, a dual balloon 234, and an inner tube 222.

The ability to place the guide catheter is a significant factor in the size of the device. For example, to perform angioplasty in the coronary arteries, which have an inner diameter of about 1½ to 4½ mm, a suitably sized guide catheter may be used. This then restricts the size of the catheter 200 which may be disposed within the guide catheter. A typical diameter of the catheter 200 may then be about 3 french or less or about 35-39 mils. The same may be placed in the femoral artery in order to be able to track to the coronary arteries in a known manner.

Analogous to these features in the catheter 100, the outer tube 203 houses the catheter 200 and may have an outside diameter of about 5 french to 7 french, and the same may be made of similar materials. The distal end of the outer tube 203 adjoins the proximal end of the dual balloon 234. The outer tube 203 provides a mounting location for an outer balloon 204, and further provides an inlet 228 for providing a fluid such as a liquid to a first interior volume 206 between the dual balloons. As noted in connection with catheter 100, an inlet 228 per se may not be necessary: the fluid, which may also be a sub-atmospheric level of air, may be provided in the first interior volume 206. Also as above, the proximal and distal ends of the volume may be sealed during manufacture. The inlet 228 may be at least partially defined by the annular volume between the interior of the outer tube 203 and the exterior of the inner tube 222.

The dual balloon 234 includes an outer balloon 204 and an inner balloon 208. These balloons are basically similar to balloons 104 and 108 described above, but may be made even smaller for use in the smaller coronary arteries.

The same types of fluids may be used as in the catheter 100.

The inner tube 222 is disposed within the interior of the dual balloon 234 and within the interior of the guide catheter 202. The inner tube 222 includes a supply lumen 220 and a return lumen 218.

A set of radio opaque marker bands 212 may be disposed on the inner tube 222 for the same reasons disclosed above in connection with the marker bands 112.

As noted above, the proximal portion of the outer balloon 204 is mounted on the outer tube 203 at its distal end. The distal end of the outer balloon 204 is secured to the distal end of the catheter 200 and along the inner tube 222. In contrast, both the proximal and distal ends of the inner balloon 208 may be secured to the inner tube 222 to create a sealed second interior volume 210.

At least two skives 224 and 226 may be defined by the inner tube 222 and employed to allow the working fluid to exit into the second interior volume 210 and to exhaust the same from the second interior volume 210.

A plurality of tabs 219 may be employed to roughly or substantially center the inner tube 222 within the catheter 200 as in catheter 100. These tabs may have the same general geometry and design as tabs 119. Of course, they may also be appropriately smaller to accommodate the smaller dimensions of this coronary artery design.

The tabs 119 and 219 are particularly important in the catheters 100 and 200, respectively, because the tabs lessen the pressure drop encountered by the fluid. Contact by the inner tube of the outer tube may also be associated with an undesired heat transfer prior to the working fluid reaching the working region, thereby deleteriously increasing the temperature of the working fluid at the working region.

The method of use of the catheter 200 is generally the same as for the catheter 100. Known techniques may be employed to place the catheter 200 into an affected coronary artery. For the catheter 200, an external guidewire may be used with appropriate attachments to the catheter.

The invention has been described above with respect to particular embodiments. It will be clear to one of skill in the art that numerous variations may be made from the above embodiments with departing from the spirit and scope of the invention. For example, the invention may be combined with stent therapies or other such procedures. The dual balloon disclosed may be used after angioplasty or may be an angioplasty balloon itself. Furthermore, while the invention has occasionally been termed herein a "cryoplasty catheter", such a term is for identification purposes only and should not be viewed as limiting of the invention. Fluids that may be used as heat transfer fluids include perfluorocarbon-based liquids, i.e., halogenated hydrocarbons with an ether bond, such as FC 72. Other materials that may be used include CFCs, Freon®, or chemicals that when placed together cause an endothermic reaction. Preferably, low viscosity materials are used as these result generally in a lessened pressure drop. The balloons may be made, e.g., of Pebax, PET/PEN, PE, PA 11/12, PU, or other such materials. Either or both of the dual balloons may be doped to improve their thermal conductivities. The shaft of inner tube 122 may be made of Pebax, PBT, PI/PEI, PU, PA 11/12, SI, or other such materials. Other variations will be clear to one of skill in the art, thus the invention is limited only by the claims appended hereto.

The invention claimed is:

1. A method of reducing restenosis after angioplasty in a blood vessel, comprising:
    inserting a catheter into a blood vessel, the catheter having a balloon;
    inflating the balloon with a perfluorocarbon such that an exterior surface of the balloon is in contact with at least a partial inner perimeter of the blood vessel, the perfluorocarbon having a temperature in the range of about −10° C. to −50° C., wherein the balloon comprises dual balloons; and
    providing a heat transfer fluid in a volume between the dual balloons.

2. The method of claim 1, further comprising the step of disposing the catheter at a desired location using at least one marker band.

3. The method of claim 1, further comprising flowing the perfluorocarbon into the balloon using a supply lumen and exhausting the perfluorocarbon from the balloon using a return lumen.

4. The method of claim 1, wherein the heat transfer fluid includes a contrast media fluid.

5. The method of claim 1, further comprising disposing the catheter such that at least a portion of the balloon is in a coronary artery.

6. The method of claim 1, further comprising disposing the catheter such that at least a portion of the balloon is in a carotid artery.

* * * * *